United States Patent [19]
Kilpela et al.

[11] Patent Number: 5,649,927
[45] Date of Patent: Jul. 22, 1997

[54] CABLE CRIMP SYSTEM

[75] Inventors: Thomas S. Kilpela; Matthew N. Songer, both of Marquette; Francis J. Korhonen, Neqaunee, all of Mich.

[73] Assignee: Pioneer Laboratories, Inc., Marquette, Mich.

[21] Appl. No.: 534,783

[22] Filed: Sep. 27, 1995

[51] Int. Cl.⁶ .................................................. A61B 17/82
[52] U.S. Cl. ........................ 606/74; 606/57; 606/103
[58] Field of Search ....................... 606/74, 103, 57, 606/61, 60, 232, 109, 151, 155, 141; 604/905; 29/282; 140/105; 220/309; 24/570, 703.1, 703.2, 703.3

[56] References Cited

U.S. PATENT DOCUMENTS

| | | | |
|---|---|---|---|
| 4,128,100 | 12/1978 | Wendorff | 606/74 |
| 4,966,600 | 10/1990 | Songer et al. | 606/74 |
| 5,116,340 | 5/1992 | Songer et al. | 606/103 |
| 5,236,434 | 8/1993 | Callicrate | 606/141 |
| 5,415,658 | 5/1995 | Kilpela et al. | 606/57 |
| 5,536,270 | 7/1996 | Songer et al. | |

*Primary Examiner*—Michael Buiz
*Assistant Examiner*—Patrick W. Rasche
*Attorney, Agent, or Firm*—Gerstman, Ellis & McMillin, Ltd.

[57] ABSTRACT

A cable winding for retention of bone in surgery having a crimp for retaining the cables together. The crimp has a bore of oval cross section, with its exterior being preferably oval in cross section as well. The cable sections extend through the single bore in side-by-side relation. Outwardly projecting flanges extend from the crimp ends for at least about 120° about the periphery to create a space between the flanges when the flanges rest on bone. This space may be used to receive the crimping jaws during the crimping process so that the crimp does not have to be forced outwardly from the bone during the crimping process. Thus, a more consistent, predetermined tension can be provided to the cable on crimping.

21 Claims, 1 Drawing Sheet

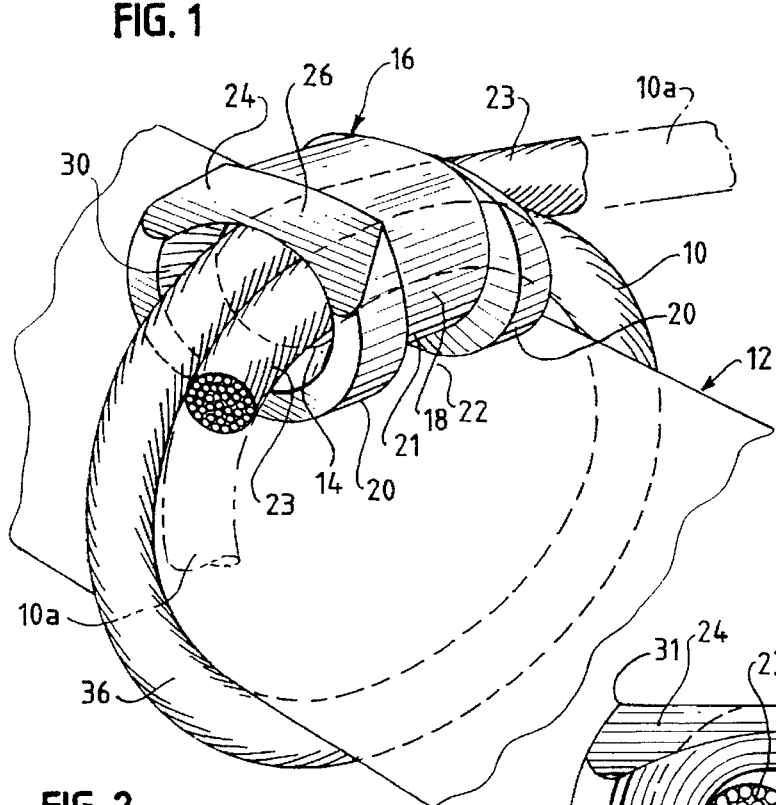
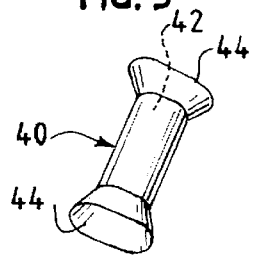
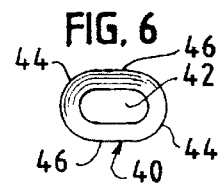
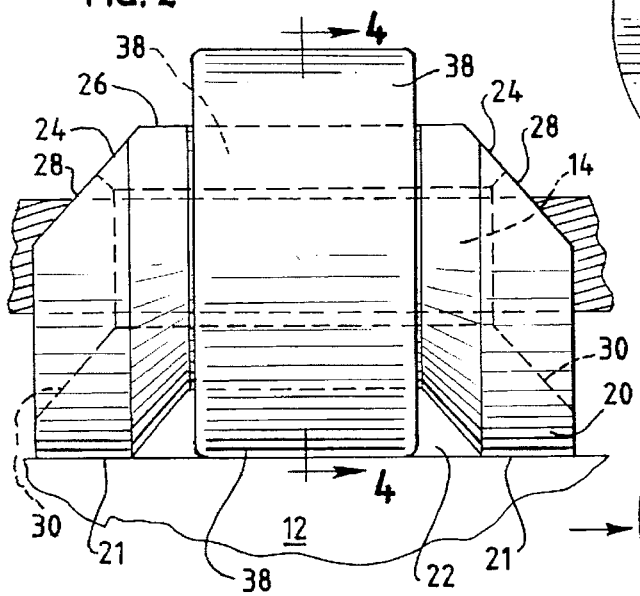
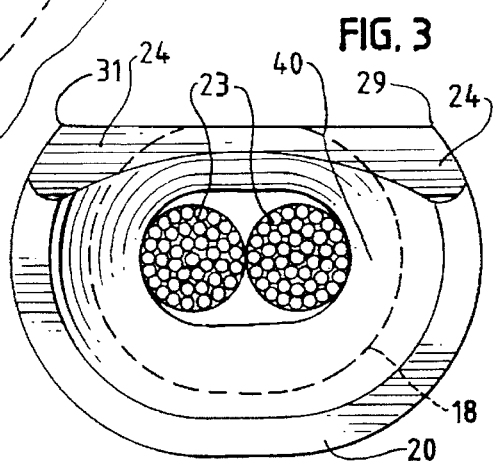
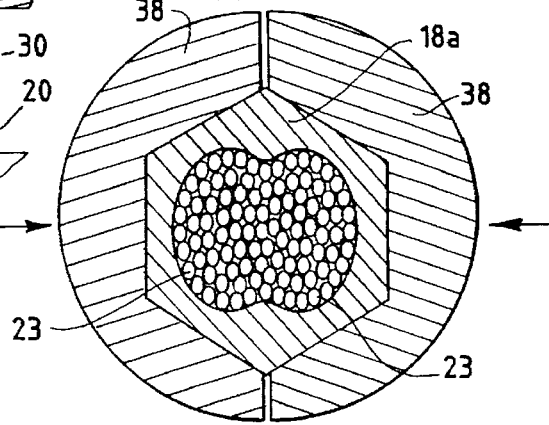

CABLE CRIMP SYSTEM

BACKGROUND OF THE INVENTION

Surgical cables positioned around bones and the like may be held in desired position by crimps, which are crushed into engagement to retain the cable at a desired position. See Kilpela et al. U.S. Pat. No. 5,415,658, and Songer et al. U.S. Pat. Nos. 4,966,600 and 5,116,340, by way of example.

Current designs of cable and crimp systems, particularly for surgical use, have significant drawbacks.

As a first drawback, there is the possibility in most cable and crimp systems for slippage of the cable in the crimp to take place. This of course can be extremely unfortunate, particularly in the orthopedic field where a crimped cable loop or winding may have been implanted in the patient to support a broken bone. With any crimp slippage, the winding or loop of cable loosens and the tension drops significantly, which can result in major pain for the patient and a bad medical outcome.

As a second drawback, many prior art crimps cannot be easily locked into a cable loop or winding at a desired tension, and then retained precisely at that tension when the crimping pliers are removed. Typically, there is an inevitable drop in the tension as the pliers are removed. Thus, a surgeon typically has to "over shoot" the desired tension, guessing how much of that tension will be lost after the crimping has been completed and the pliers removed. This brings in the significant possibility for tensioning errors. A tension which is too low or a tension which is too high on orthopedic cables can give a bad medical result.

By this invention, a new crimp is provided in which a crimp exhibits better cable retention at lower crimping pressures (as exerted by the crimping pliers), other things being equal. Additionally, the crimping system of this invention, in a preferred form, can provide a more accurate tension to the cable so that there is little or no need to "overshoot" the tensioning of the cable, with the expectation that some of the tension will be lost after the crimp has been applied by the crimping pliers to a cable loop or winding.

DESCRIPTION OF THE INVENTION

In accordance with this invention a malleable, tubular crimp is provided for securing a plurality (typically two) cable portions together. The crimp defines a bore of generally oval cross-section extending entirely through the crimp, to permit a plurality of cable portions to extend therethrough in side-by-side relation. An advantage is conferred by this invention in that, when a pair or more of cable portions (which are generally multistrand in nature) are pressed together in a single oval bore by the crimping action, the irregular surface of the multistrand cable sections, resulting from the multiple strands, tend to nest and mesh together, providing a locking action between the two cable portions that serves to reinforce and enhance the retaining action which is naturally provided by the crimp itself. Thus, it has been found that crimps of greatly increased retention strength can be provided, when compared with other crimp designs where the crimping pressure applied by the crimping pliers is the same.

The crimp also may have a pair of opposed ends which each define an outwardly projecting flange from the tube. This flange may merely comprise a pair of opposed projections or ears, with each projection occupying about 20 to 90 degrees of the circumference of the crimp, and with typically no other outwardly projecting flange between them on the periphery of the end. This can be made by flaring the crimp ends and flattening the crimp to oval cross-section.

Alternatively, a tubular crimp of generally oval bore may be provided having typically a single outwardly projecting flange at each end which extends at an arc angle of at least about 120 degrees (and preferably less than 360 degrees) about a first side of the crimp. Thus, the crimp flanges at the crimp ends may rest against a bone while the crimp retains a cable loop or winding, to provide a space for crimping jaws between a central portion of the first side of the crimp and the bone. Conventional crimping jaws may enter the space, to surround a central portion of the crimp of this invention to crush it inwardly from substantially all directions. A portion or portions of the jaws reach into the space underneath the crimp during the crimping process, between the crimp and the bone, occupying the space described above, to provide superior crimping action.

The respective end flanges may have sharp edges which dig into the bone in a manner similar to the disclosure of Kilpela et al. U.S. Pat. No. 5,415,658, or they may have blunt contact surfaces against the bone.

The generally oval bore of the crimp may be positioned so that the cross-sectional major axis of the oval bore is generally in longitudinal relation with the first side of the crimp, which first side is spaced from the bone by the respective flanges.

While the respective crimp flanges may extend a full 360 degrees about the crimp if desired, an advantage is achieved by removing the outwardly facing portions of the flanges (that face away from the bone). The advantage of that is that the maximum spacing of remote portions of the crimp from the bone can thus be reduced, so that the "profile" of the crimp is minimized. This can reduce tissue irritation and the like for a surgically implanted cable and crimp system.

Accordingly, it becomes possible to secure a cable wrapped around bone at a predetermined tension by a process which comprises: placing a pair of first cable portions through a bore of a malleable metal, tubular crimp, with the cable portions being attached to opposed ends of a central cable portion wrapped around the bone. One also positions the crimp so that a pair of opposed crimp end flanges rest on the bone to define a space between a central portion of the crimp and the bone. One then tensions the cable to a predetermined tension, placing crimping jaws around the crimp with at least one, and preferably portions of both of the crimping jaws, occupying the space, so that essentially the entire periphery of the crimp can be enclosed within the crimping jaws. One then crimps (inwardly collapses) the crimp to secure the first cable portions within the crimp in a manner which is strong enough to maintain the predetermined tension.

Furthermore, because of the presence of the space between the crimp and the bone, it is possible to insert the crimping jaws into crimping relation without causing the crimp flanges to lose contact with the bone. Thus, after the crimping has taken place, the crimping jaws can be removed without any loss of cable tension.

To the contrary, in the prior art, crimping jaws are sometimes slid between a crimp of a cable winding and the bone, forcing the crimp and attached cable outwardly so that the jaws can surround and crush the crimp. Then, when the jaws are removed, the crimp and cable naturally springs back into its original position against the bone, which can result in a significant loss of cable tension, so that it is necessary to overshoot the cable tension during the cable application and crimping process in an undesirable manner, which is no longer needed in accordance with this present invention.

As a further advantage, the outwardly projecting end flanges facilitate the proper positioning of the crimping pliers jaws to encompass the central, barrel portion of the crimp, to eliminate an accidental, improper crimping position in which the crimping is ineffective. The flanges bracket the jaws and thus hold the crimp in proper position in the jaws.

DESCRIPTION OF DRAWINGS

In the drawings, FIG. 1 is an enlarged, perspective view of a cable loop surrounding a bone, with portions of the cable being retained together in a common, single bore of the crimp;

FIG. 2 is a side elevational view of the crimp shown in FIG. 1 and further showing the pliers jaws;

FIG. 3 is an end elevational view of the crimp shown in FIG. 1, with the retained cable portions being shown in section, prior to crimping by the pliers; and FIG. 4 is a transverse sectional view taken along line 4—4 of FIG. 3, showing the central portion thereof after it has been crushed into crimped position by the crimping pliers.

FIG. 5 is a perspective view of another embodiment of a cable crimp of this invention.

FIG. 6 is an end elevational view of the cable crimp of FIG. 5.

DESCRIPTION OF SPECIFIC EMBODIMENTS

Referring to FIGS. 1–3, a crimp and cable system is shown comprising a length of multistrand metal cable 10 defining a loop wrapped around a broken bone 12 to secure it, with two sections of the cable occupying a single, oval bore 14 of tubular crimp 16. Tubular crimp 16, as shown, defines a central portion 18 which defines oval bore 14 and also has an oval exterior wall.

Crimp 16 defines a pair of outwardly extending flanges 20 having an outer edge portion 21 that rests against bone 12 to provide a space 22 between bone 12 and the central, tubular portion 18 of the crimp. Each flange portion 21 may extend radially beyond central portion 18, generally by at least about 0.02 inch and typically about 0.029 inch, a distance to define a space 22 sufficient to receive a crimping pliers jaw.

Outer portions 24 of the flanges have been cut away as shown to reduce the height or profile of crimp 16 relative to the bone, to reduce the disruptive effect that crimp 16 may have on surrounding tissue.

Such crimp and cable systems are used in a variety of ways, particularly in the field of orthopedic surgery, for the retention of bones and bone structures comprising a plurality of bones, typically on a permanent basis, with the crimp and cable system being implantable for permanent residence in the patient. Cable and crimp systems may be used in severe breaks of bones, or for reconstitution of the sternum after heart surgery, or the like.

The portion of cable 10 that is shown in full lines in FIG. 1 indicates that portion of the cable which is typically retained in the long term implantation. However, during the actual implantation of the cable and crimp, longer end sections 10a, shown in dotted line, are provided to the cable. These sections can extend to a known tensioner member or the like, by means of which a desired tension may be imposed on the cable prior to crushing crimp 16 into its cable retaining position. Then, cable portions 10a may be cut away by the surgeon, leaving the remaining cable portion 10 as shown, which typically resides permanently in the patient.

Crimp 16 may be manufactured from a length of tubular, malleable metal of a conventional composition. First, the tube and especially central portion 18 may be crushed into an oval configuration while also allowing oval end flanges 20 to form. Then, a cut along surface line 26 may be provided by means of a machine tool, followed by 45° angle cuts 28 of the flange 20 that was formed in the first machining step. Angled surfaces 30 at the respective ends of bore 14 facilitate the insertion of the cable portions into the crimp.

It can be seen that the respective crimp flanges 20 at each end have a peripheral extent about the longitudinal axis 32 of less than 360°, preferably defining an arc angle of about 180° to 270°, and typically about 200° to 250°, as illustrated by the arc angle of about 240° from point 29 clockwise on flange 20 around to point 31 (FIG. 3), i.e., about ⅔ of a complete, 360° loop. The arc angle may be measured by the angle between radii extending from the longitudinal axis of the crimp to the ends 29, 31 of the arc of the flange being measured.

By this invention, the crimping process may be accomplished by placing a pair of first cable portions 23 through bore 14 of the malleable metal, tubular crimp. Cable portions 23 are integrally connected to opposed ends of central cable portion 36 which is wrapped around bone 12, so that crimping of the first cable portions 23 secures the loop around the bone.

Alternatively, the cable portion 36 may be a complex winding through a complex array of bones, a multiple loop, or any other desired configuration.

One positions crimp 16 so that the pair of opposed crimp end flanges 20 rest on the bone 12 to define the space 22 between central portion 18 of the crimp and bone 12.

The cable is then tensioned, typically by pulling of cable sections 10a with a known cable tensioner apparatus at a predetermined tension. Then, one places crimping jaws 38 (FIGS. 2 and 4) of typically conventional design, around the crimp. In this embodiment, the oval cross section of the crimp is positioned so that major axis 40 is positioned generally parallel to the bone 12, and crimping jaws 38 are positioned to surround central crimp portion 18 and to move with crimping action in a direction generally parallel to major axis 40. Both of the crimping jaws 38 enter space 22, moving toward each other within said space as the central portion 18 of crimp is crushed together from substantially all directions (FIG. 4) into a structure 18a of generally hexagonal cross-sectional shape, as governed by the shape the crimping jaws 38. Because the respective cable portions 23 are crushed together, the various surface strands of the cable portions nest in the irregularities of the surface of the other cable portion, providing a very strong bond which resists sliding relative to each other and the crimp. Because the crimping jaws can fit underneath central crimp portion 18 without lifting the crimp out of its engagement with bone 12, the tension imposed on cable 10 exhibits little variance as the crimping process takes place, so that the desired tension is provided to the cable after the crimp is crushed into retaining relation. Then, crimp 16 sits on the bone, retaining the cable loop with the desired tension, and having a lower profile or height from that which is achieved by a crimp having a flange with a 360° extent.

At least in part because of the interlocking of the cable portions 23 within the crimp, the crimping force from jaws 38 needed to achieve the same holding power for the crimp of this invention is much less than a crimp having two separate bores for lengths of cable.

Referring to FIGS. 5 and 6, another embodiment of a cable crimp 40 is shown. Cable crimp 40 may be made of a malleable metal tube having a generally oval cross section and a single lumen or bore 42. In this embodiment, the crimp 40 defines a pair of spaced, opposed, outwardly extending flanges 44 which flanges intersect the major axis of the oval cross-section. At the ends of the body of crimp 40 which are adjacent to the minor axis of the oval cross-section, such as areas 46, there is essentially no flange. One sees only the thickness of the wall of crimp 40 in FIG. 6 at that area 46.

Crimp 40 may be made from a cylindrical-tube of malleable metal by crushing the tube into oval shape, and then flaring out the respective spaced flanges 44 with an appropriate tool. Such a crimp will tend to center and seat itself properly in a pair of crimping pliers without sliding to one side or the other. Thus, such a crimp may be loosely held in the jaws of crimping pliers and inserted into the incision for application to a cable without the surgeon having to worry whether the crimp has slipped to one side or the other. Also, a pair of cables may be held within the crimp lumen or bore 42 and crushed together in the manner previously described for improved cable retention. Flanges 44 typically occupy from about 30° to 90° of the circumference of the crimp with the arc angle of each flange being measured as previously described by the angle of radii extending from the longitudinal axis of the crimp to the respective flange ends.

The above has been offered for illustrative purposes only, and is not intended to limit the scope of the invention of this application, which is as defined in the claims below.

That which is claimed is:

1. A malleable metal, tubular crimp for securing a plurality of cable portions together, said crimp defining a bore of generally oval cross-section extending entirely through said crimp to permit a plurality of said cable portions to extend therethrough in side-by-side relation, said crimp having a pair of opposed ends which each define an outwardly projecting flange extending at least about 120° but only partially about opposed ends of said crimp, said flanges extending outwardly from said crimp by a distance of at least about 0.02 inch, whereby said flanges may rest against a bone while providing spacing for crimping jaws between a central portion of said crimp and said bone.

2. The crimp of claim 1 in which said generally oval bore defines major and minor cross-sectional axes, said major axis being in generally longitudinal relation with said first side.

3. The crimp of claim 1 in which said crimp flanges extend in an arc angle of about 180° to 270° about said crimp ends.

4. The crimp of claim 1 which has an outer surface between said flanges that is generally oval in cross section.

5. The crimp of claim 1 in which said crimp flanges extend in an arc angle of about 200° to 250° about said crimp ends.

6. In combination, a cable winding, a crimp, and crimping pliers, said cable winding being adapted to be placed about a bone, said cable winding having first cable portions which extend through a single bore of said crimp, said bore being of generally oval cross-section and extending entirely through said crimp with said cable portions extending through said bore in side-by-side relation, said crimp having a pair of opposed ends which each define an outwardly projecting flange about opposed ends of a first side of said crimp, said flanges being adapted to be in contact with said bone to cause a space to be created between most of said first side and said bone; said crimp being carried in jaws of said crimping pliers, a portion of at least one of said jaws extending into said space while the flanges are in contact with said bone, to permit said crimp to be crushed by the crimping pliers to secure said cable portions within said crimp while the flanges remain in contact with said bone.

7. The crimp of claim 6 in which said generally oval bore defines major and minor cross-sectional axes, said major axis being in generally in longitudinal relation with said first side.

8. The crimp of claim 7 in which said crimp flanges extend about 120° to 270° about said crimp ends.

9. The crimp of claim 8 which has an outer surface between said flanges that is generally oval in cross section.

10. A malleable metal, tubular crimp for securing a plurality of cable portions together, said crimp defining a bore of generally oval cross-section extending entirely through said crimp to permit a plurality of said cable portions to extend therethrough in side-by-side relation, said crimp having a pair of opposed ends which each define an outwardly projecting flange extending in an arc angle of about 180° to 250° about opposed ends of a first side of said crimp, in which said generally oval bore defines major and minor cross-sectional axes, said major axis being in generally longitudinal relation with said first side, whereby said crimp flanges may rest against a bone to provide spacing for crimping jaws between a central portion of the first side of said crimp and said bone.

11. The crimp of claim 10 which has an outer surface between said flanges that is generally oval in cross section.

12. A method of securing a cable wrapped around bone at a predetermined tension, which comprises: placing a pair of first cable portions through a bore of a malleable metal, tubular crimp, said cable portions being positioned at opposed ends of a central cable portion wrapped around the bone, while positioning said crimp so that a pair of opposed crimp end flanges rest on the bone to define a space between a central portion of the crimp and the bone; tensioning said cable to a predetermined tension; placing crimping jaws around said crimp with at least one of said crimping jaws occupying said space while said flanges remain in contact with the bone; and crimping said crimp to secure said first cable portions in the crimp in a manner strong enough to maintain said tension.

13. The method of claim 12 in which said bore is of generally oval cross section having a major cross-sectional axis that extends generally parallel to said bone at the vicinity of said space.

14. The method of claim 13 in which said crimping jaws substantially surround said crimp and close in a direction generally parallel to said major axis.

15. The method of claim 12 in which said crimping takes place within said jaws without the crimp flanges losing contact with said bone.

16. The method of claim 12 in which said crimp has only a single bore.

17. The method of claim 12 in which said end flanges each extend only partially around said crimp to reduce the maximum spacing of remote portions of said crimp from said bone.

18. The method of claim 12 in which portions of both crimping jaws extend into said space during said crimping.

19. The method of claim 18 in which said bore is of generally oval cross section having a major cross-sectional axis that extends generally parallel to said space.

20. The method of claim 19 in which said crimp has only a single bore.

21. The method of claim 20 in which said end flanges each extend only partially around said crimp to reduce the maximum spacing of remote portions of said crimp from said bone.

* * * * *